United States Patent

Tagami et al.

Patent Number: 5,089,026
Date of Patent: Feb. 18, 1992

[54] DYEING COMPOSITION FOR KERATIN FIBER

[75] Inventors: Hidetoshi Tagami, Chiba; Jiro Kawase, Funabashi, both of Japan

[73] Assignee: Kao Corporation, Tokyo, Japan

[21] Appl. No.: 691,285

[22] Filed: Apr. 25, 1991

[30] Foreign Application Priority Data

Apr. 27, 1990 [JP] Japan .................. 2-112594

[51] Int. Cl.⁵ .............................................. A61K 7/13
[52] U.S. Cl. ........................................ 8/435; 8/405; 8/406; 8/408; 8/409; 8/414; 8/415; 8/416; 424/70
[58] Field of Search ............... 8/405, 406, 408, 409, 8/414, 415, 416, 435; 424/70

[56] References Cited

U.S. PATENT DOCUMENTS

| | | | |
|---|---|---|---|
| 3,861,868 | 1/1975 | Milbrada ..................... | 8/410 |
| 3,957,424 | 5/1976 | Zeffren et al. ............... | 8/416 |
| 4,318,901 | 3/1982 | Ishida et al. ................ | 8/405 |
| 4,994,087 | 2/1991 | Konrad et al. ............... | 8/409 |
| 5,009,880 | 4/1991 | Grollier et al. .............. | 8/407 |
| 5,015,260 | 5/1991 | Tamura et al. ............... | 8/408 |

*Primary Examiner*—Paul Lieberman
*Assistant Examiner*—Williams S. Parks
*Attorney, Agent, or Firm*—Sughrue, Mion, Zinn, Macpeak & Seas

[57] ABSTRACT

A dyeing composition for a keratin fiber which comprises 1,5-dihydroxynaphthalene as a coupling substance, 2-amino-5-hydroxybenzoic acid or a cosmetically acceptable salt thereof as a color developing substance, and a cosmetically acceptable base is disclosed. The dyeing composition for a keratin fiber give a vivid red color tone having a high chroma and an extremely high fastness.

11 Claims, No Drawings

DYEING COMPOSITION FOR KERATIN FIBER

FIELD OF THE INVENTION

This invention relates to a dyeing composition for a keratin fiber. More particularly, it relates to a dyeing composition for a keratin fiber which can give a vivid red color tone and an extremely high fastness.

BACKGROUND OF THE INVENTION

In order to dye keratin fibers including hair, so-called oxidation dyeing compositions, wherein a color developing substance is used together with a coupling substance, have been widely used. In these oxidation dyeing compositions, a so-called oxidation dyestuff formed by the oxidative coupling between a color developing substance and a coupling substance would intensely dye, for example, the hair. Common examples of the color developing substance include p-phenylenediamine derivatives, p-aminophenol derivatives, diaminopyridine derivatives, 4-aminopyrazolone derivative and heterocyclic pyrazolones, while common examples of the coupling substance include m-phenylenediamine derivatives, phenol derivatives, m-aminophenol derivatives and pyrazolone derivatives.

However conventional oxidation dyeing compositions are still unsatisfactory in chroma, dyeing power and fastness.

SUMMARY OF THE INVENTION

Under these circumstances, the present inventors have conducted extensive studies on a combination of a color developing substance with a coupling substance in order to solve the above-mentioned problems. As a result, they have found that a keratin fiber can be dyed into a vivid red color tone of a high chroma by using a specific naphthalene derivative as a coupling substance together with a specific aminophenol derivative as a color developing substance and that the keratin fiber thus dyed has a high fastness against shampooing, thus completing the present invention.

Accordingly, the present invention provides a dyeing composition for a keratin fiber, which comprises 1,5-dihydroxynaphthalene as a coupling substance, 2-amino-5hydroxybenzoic acid or a cosmetically acceptable salt thereof as a color developing substance, and a cosmetically acceptable base.

DETAILED DESCRIPTION OF THE INVENTION 1,5-Dihydroxynaphthalene contained in the dyeing composition for a keratin fiber of the present invention (hereinafter referred to simply as "dyeing composition") as a color developing substance may be synthesized by, for example, a method described in *Beilstein* 14, IV, 2080.

2-amino-5-hydroxybenzoic acid can be used in the dyeing composition of the present invention in the form of a cosmetically acceptable salt thereof in order to improve handling properties during the preparation of the dyeing composition. Such a cosmetically acceptable salt include salts with an inorganic acid such as hydrochloric acid, sulfuric acid, phosphoric acid and the like; and an organic acid such as acetic acid, propionic acid, lactic acid, citric acid and the like.

In the dyeing composition of the present invention, though one of 1,5-dihydroxynaphthalene (i.e., a coupling substance) and 2-amino-5-hydroxybenzoic acid or a cosmetically acceptable salt thereof may be contained in excess to another, 1,5-dihydroxynaphthalene and 2-amino-5-hydroxybenzoic acid or a cosmetically acceptable salt thereof are contained at a molar ratio of preferably from 1 : 0.5 to 1 : 2.0, more preferably from approximately 1 : 0.8 to 1 : 1.5.

The dyeing composition of the present invention may further contain, for example, other oxidation dye(s) obtained from a known color developing substance and a known coupling substance and a common direct dye, if required, to thereby achieve the desired color tone.

Examples of the coupling substance include α-naphthol, o-cresol, m-cresol, 2,6-dimethylphenol, 2,5-dimethylphenol, 3,4-dimethylphenol, 3,5-dimethylphenol, benzcatechin, pyrogallol, 1,7-dihydroxynaphthalene, 5-amino-2-methylphenol, hydroquinone, 2,4-diaminoanisole, m-tolylene-diamine, 4-aminophenol, resorcin, resorcin monomethyl ether, m-phenylenediamine, 1-phenyl-3-methyl-5-pyrazolone, 1-phenyl-3-amino-5-pyrazolone, 1-phenyl-3,5-diketopyrazolidine, 1-methyl-7-dimethylamino-4-hydroxyquinolone-2,1-amino-3-acetylacetamino-4-nitrobenzol, 1-amino-3-cyano-acetylamino-4-nitrobenzol, m-aminophenol, 4-chlororesorcin, 2-methylresorcin, 2,4-diaminophenoxyethanol, 3,5-diaminotrifluoromethylbenzene, 2,4-diaminofluorobenzene, 3,5-diaminofluorobenzene, 2,6-diaminopyridine, 2,4-diamino-6-hydroxypyrimidine, 2,4,6-triaminopyrimidine, 2-amino-4,6-dihydroxypyrimidine, 4-amino-2,6-dihydroxypyrimidine, 4,6-diamino-2-hydroxypyrimidine, p-nitro-o-phenylenediamine, 2-amino-5-nitrophenol, p-nitro-m-phenylenediamine, o-nitro-p-phenylenediamine and 2-amino-4-nitrophenol.

Examples of the color developing substance include compounds having one or several $NH_2$- groups and/or $NHR_1$—or $N(R_1)_2$—group(s), wherein R represents an alkyl group or a hydroxyalkyl group having 1 to 4 carbon atoms such as p-phenylenediamine, p-tolylenediamine, N-methyl-p-phenylenediamine, N,N-dimethyl-p-phenylenediamine, N,N-diethyl-2-methyl-p-phenylenediamine, N-ethyl-N-(hydroxyethyl)-p-phenylenediamine, chloro-p-phenylenediamine, N,N-bis(2-hydroxyethyl)-p-phenylenediamine, methoxy-p-phenylenediamine, 2,6-dichloro-p-phenylenediamine, 2-chloro-6-bromo-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine, N-2-methoxyethyl-p-phenylenediamine; 2,5-diaminopyridine derivatives and N-butyl-N-sulfobutyl-p-phenylenediamine.

The dyeing composition of the present invention would undergo oxidative coupling in the presence of oxygen in the atmosphere to thereby dye, for example, the hair. It is preferable, however, to add a chemical oxidizing agent thereto so as to induce the oxidative coupling. In such a case, the dyeing composition of the present invention can be provided as a first compartment of a dyeing kit for keratin fibers and the oxidizing agent can be provided as a second compartment of the dyeing kit. Examples of particularly preferable oxidizing agents include hydrogen peroxide; products obtained by adding hydrogen peroxide to urea, melamine or sodium borate; and mixtures of such a hydrogen peroxide adduct with potassium peroxide/disulfuric acid.

It is usually preferable to provide the dyeing composition of the present invention in the form of, for example, cream, emulsion, gel or solution. These products may be prepared by adding, for example, a cosmetically acceptable base which comprises water, wetting agent (emulsifier), solubilizer, thickener, stabilizer, texture improver, hair styling base and/or perfume, each commonly used in the field of cosmetic, to the color developing substance and the coupling substance, and then treating the obtained mixture in a conventional manner. Examples of the wetting agent (emulsifier) to be used herein include alkyl benzenesulfonates, fatty alcohol sulfates, alkyl sulfonates, fatty acid alkanol amides and products obtained by adding ethylene oxide to fatty alcohols. Examples of the thickener include methylcellulose, starch, higher fatty alcohols, paraffin oil and fatty acids. Examples of the stabilizer include reducing agents such as sulfites, hydroquinone derivatives and chelating agents. Examples of the texture improver and hair styling base include oils such as silicone, higher alcohols and various nonionic surfactants and various cationic polymers.

The total content of 2-amino-5-hydroxybenzoic acid or a cosmetically acceptable salt thereof and 1,5-dihydroxynaphthalene in the dyeing composition of the present invention may preferably range from 0.1 to 3 % by weight, in particular, from 0.2 to 2 % by weight, based on the total weight of the composition.

The total content of the coupling substances including known coupling substance and the color developing substances including known color developing substances in the dyeing composition of the present invention may preferably range from 0.1 to 5 % by weight, in particular, from 1 to 3 % by weight, based on the total weight of the composition.

The contents of the wetting agent (emulsifier) and the thickener may preferably range respectively from 0.5 to 30 % by weight and from 0.1 to 25 % by weight, based on the total weight of the composition, in general.

The total content of other oxidation dye(s) and/or direct dye(s), if employed, in the dyeing composition of the present invention may preferably range from 0.1 to 15 % by weight, more preferably from 1 to 8 % by weight, based on the total weight of the composition. Further, the pH value of the whole composition may be preferably adjusted to 6 to 11, more preferably adjusted to 8 to 10.

A keratin fiber may be dyed with the dyeing composition of the present invention by applying to the fibers an appropriate amount of the dyeing composition of the present invention for a period of time sufficient to dye the fiber. More specifically, the keratin fiber can be dyed by, for example, the following method. Namely, an oxidizing agent is added to the dyeing composition of the present invention to thereby effect oxidative coupling. The dyeing solution thus obtained is then applied to the keratin fiber. After a working period of approximately 5 to 50 minutes, preferably 25 to 35 minutes, the keratin fiber is washed and dried. The application of the dyeing solution to the keratin fiber may be performed at a temperature of from 15 to 40° C.

A keratin fiber can be dyed with the dyeing composition of the present invention into a vivid red color of a high chroma. The color tone thus obtained is highly fast to light, washing and rubbing.

To further illustrate the present invention, and not by way of limitation, the following Examples will be given.

EXAMPLE 1

To 100 g of a base having the composition as specified below, were added 0.01 mol of the color developing substance and 0.01 mol of the coupling substance, each specified in the following items (1) and (2) and Table 1. Next, the pH value of the obtained composition was adjusted to 9.5 with ammonia. Thus a dyeing composition was obtained.

To 100 g of the dyeing composition, was added the same weight of a 6 % by weight aqueous solution of hydrogen peroxide to thereby give a dyeing solution. The dyeing solution thus obtained was applied to goat hair and then allowed to stand at 30° C for 30 minutes. Then the goat hair thus dyed was washed with a common shampoo and dried. The color tone and chroma of the dyed hair were evaluated based on the criteria as given below. Table 1 shows the results.

In order to examine the fastness to shampooing, the dyed hair obtained above was repeatedly shampooed and dried at room temperature 10 times. Then the degree of fading was compared to that observed before shampooing with the naked eye and evaluated based on the criteria as given below. Table 1 shows the results.

| Base composition: | (% by weight) |
|---|---|
| oleic acid | 10 |
| oleic acid diethanolamide | 8 |
| oleyl alcohol | 2 |
| polyoxyethylene octyldodecyl ether (average mole number of added EO: 20) | 10 |
| ethanol | 15 |
| propylene glycol | 10 |
| ammonium chloride | 3 |
| 25% ammonia | 7 |
| water | 35 |

(1) Color developing substance $P_1$: 2-amino-5-hydroxybenzoic acid (2) Coupling substance $C_1$: 1,5-dihydroxynaphthalene
$C_2$: p-amino-o-cresol
$C_3$: 1-naphthol (a) Criteria for evaluating chroma:

A: good
B: usual
C: poor (b) Criteria for evaluating fastness to shampooing:

A: scarcely any fading
B: somewhat fading
C: serious fading

TABLE 1

| | Dyeing Composition | | |
|---|---|---|---|
| | Product of the Invention | Comparative Product 1 | Comparative Product 2 |
| Color developing Substances | $P_1$ | $P_1$ | $P_1$ |
| Coupling Substance | $C_1$ | $C_2$ | $C_3$ |
| Hair-dyeing trace: | | | |
| Color tone | Red | Yellow brown | Yellow Brown |
| (a) Chroma | A | C | C |
| (b) Fastness to | A | C | B |

TABLE 1-continued

| | Dyeing Composition | | |
|---|---|---|---|
| | Product of the Invention | Comparative Product 1 | Comparative Product 2 |
| Shampooing | | | |

While the invention has been described in detail and with reference to specific examples thereof, it will be apparent to one ordinary skilled in the art that various changes and modifications can be made therein without departing from the spirit and scope thereof.

What is claimed is:

1. A dyeing composition for a keratin fiber, which comprises 1,5-dihydroxynaphthalene, 2-amino-5-hydroxybenzoic acid or a cosmetically acceptable salt thereof and a cosmetically acceptable base.

2. A dyeing composition of claim 1, wherein the total content of 1,5-dihydroxynaphthalene and 2-amino-5-hydroxybenzoic acid or a cosmetically acceptable salt thereof ranges from 0.1 to 3 % by weight based on the total weight of the composition.

3. A dyeing composition of claim 1, wherein 1,5-dihydroxynaphthalene and 2-amino-5-hydroxybenzoic acid or a cosmetically acceptable salt thereof are contained at a molar ratio of from 1 : 0.5 to 1 : 2.0.

4. A dyeing composition of claim 1, wherein 1,5-dihydroxynaphthalene and 2-amino-5-hydroxybenzoic acid or a cosmetically acceptable salt thereof are contained at a molar ratio of from 1 : 0.8 to 1 : 1.5.

5. A dyeing composition of claim 1, wherein said cosmetically acceptable base comprises at least one selected from water, wetting agent, solubilizer, thickener, stabilizer, texture improver, hair styling base and perfume.

6. A dyeing composition of claim 1, wherein the pH value of the composition ranges from 6 to 11.

7. A dyeing composition of claim 1, wherein said cosmetically acceptable salt is a salt of hydrochloric acid, sulfuric acid, phosphoric acid, acetic acid, propionic acid, lactic acid or citric acid.

8. A process for dyeing keratin fibers, which comprises steps of applying to the fibers an effective amount of a composition comprising 1,5-dihydroxynaphthalene, 2-amino-5-hydroxybenzoic acid or a cosmetically acceptable salt thereof and a cosmetically acceptable base for a period of time sufficient to dye the fiber.

9. A process of claim 8, wherein an oxidizing agent is added to said composition.

10. A dyeing kit for keratin fibers comprising:
    a first compartment comprising 1,5-dihydroxynaphthalene, 2-amino-5-hydroxybenzoic acid or a cosmetically acceptable salt thereof and a cosmetically acceptable base, and
    a second compartment comprising an oxidizing agent.

11. A process for dying human hair comprising applying a dyeing composition comprising 1,5-dihydroxynaphthalene, 2-amino-5-hydroxybenzoic acid or a cosmetically acceptable salt thereof and a cosmetically acceptable base to human hair.

* * * * *